(12) United States Patent
Wu et al.

(10) Patent No.: US 8,372,312 B1
(45) Date of Patent: Feb. 12, 2013

(54) NON-SYMMETRICAL DIBENZODITHIENOTHIOPHENE COMPOUNDS

(75) Inventors: Yiliang Wu, Oakville (CA); Ping Liu, Mississauga (CA); Anthony James Wigglesworth, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 13/274,484

(22) Filed: Oct. 17, 2011

(51) Int. Cl.
*H01B 1/00* (2006.01)
*H01L 29/08* (2006.01)
*H01L 51/40* (2006.01)

(52) U.S. Cl. .............................. 252/500; 257/40; 438/99
(58) Field of Classification Search .................. 252/500; 257/40; 438/99
See application file for complete search history.

(56) References Cited

U.S. PATENT DOCUMENTS

2008/0283828 A1* 11/2008 Lee et al. ......................... 257/40

FOREIGN PATENT DOCUMENTS

| JP | 2010-177641 | 12/2010 |
| WO | WO 2011/004869 A1 | 1/2011 |

OTHER PUBLICATIONS

Jianhua Gao, Rongjin Li, Liqiang Li, Qing Meng, Hui Jiang, Hongxiang Li and Wenping Hu, "High-Performance Field-Effect Transistor Based on Dibenzo[d,d']thieno[3,2-b;4,5-b']dithiophene, an Easily Sythesized Semiconductor with High Ionization Potential," Advanced Materials, 2007, pp. 3008-3011, vol. 19, 2007 WILEY-VCH Verlag GmbH & Co. KGaA. Weinheim.

Shoji Shinamura, Itaru Osaka, Eigo Miyazaki, Akiko Nakao, Masakazu Yamagishi, Jun Takeya and Kazuo Takimiya, "Linear- and Angular-Shaped Naphthodithiophenes: Selective Synthesis, Properties, and Application to Organic Field-Effect Transistors," Journal of the American Chemical Society, 2011, pp. 5024-5035, vol. 133, 2011 American Chemical Society, ACS Publications.
Jangdae Youn, Ming-Chou Chen, You-Jhih Liang, Hui Huang, Rocio Ponce Ortiz, Choongik Kim, Charlotte Stern, Tarng-Shiang Hu, Liang-Hsiang Chen, Jing-Yi Yan, Antonio Facchetti and Tobin J. Marks, "Novel Semiconductors Based on Functionalized Benzo[d,d']thieno[3,2-b;4,5-b']dithiophenes and the Effects of Thin Film Growth Conditions on Organic Field Effect Transistor Performance," Chemistry of Materials, 2010, pp. 5031-5041, vol. 22, 2010 American Chemical Society.
U.S. Appl. No. 13/158,584, filed Jun. 13, 2011; Title: Electronic Device; Inventors: Yiliang Wu et al.
Rongjin Li, Lang Jiang, Qing Meng, Jianhua Gao, Hongxiang Li, Qingxin Tang, Meng He, Wenping Hu, Yunqi Liu and Daoben Zhu, "Micrometer-Sized Organic Single Crystals, Anisotropic Transport, and Field-Effect Transistors of a Fused-Ring Thienoacene," Advanced Materials, 2009, pp. 4492-4495, vol. 21, 2009 WILEY-VCH Verlag GmbH & Co. KgaA, Weinheim.

* cited by examiner

Primary Examiner — Mark Kopec
Assistant Examiner — Jaison Thomas
(74) Attorney, Agent, or Firm — Fay Sharpe LLP (57) ABSTRACT

Disclosed herein is an asymmetrical semiconducting compound of Formula (I):

Formula (I)

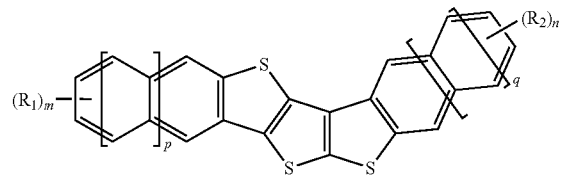

wherein $R_1$ and $R_2$ are as described herein. The compound is useful in a semiconducting layer for an electronic device, such as a thin-film transistor. Devices including the compound exhibit high mobility and excellent stability.

20 Claims, 3 Drawing Sheets
(1 of 3 Drawing Sheet(s) Filed in Color)

NON-SYMMETRICAL DIBENZODITHIENOTHIOPHENE COMPOUNDS

BACKGROUND

The present disclosure relates to semiconducting compounds that provide high electrical performance, are soluble, and are air stable. Such compounds are useful in thin-film transistors (TFTs) and/or other electronic devices comprising a semiconducting layer. Methods of making such compounds and using them are also disclosed herein.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility (also referred to as the charge carrier mobility) and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, inkjet printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility. It would be desirable to develop new compounds that overcome these challenges.

BRIEF DESCRIPTION

Disclosed in various embodiments are semiconducting compounds that are useful in electronic devices. The compounds are non-symmetrical or asymmetrical dibenzodithienothiophenes or dinaphthodithienothiophenes.

Disclosed in embodiments is a semiconducting compound having the structure of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 6; n is the number of $R_2$ sidechains and is an integer from 0 to 6; and p and q are independently 0 or 1.

In more specific embodiments, the semiconducting compound may have the structure of Formula (II):

Formula (II)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 4; and n is the number of $R_2$ sidechains and is an integer from 0 to 4. The structure of Formula (II) is obtained when both p and q are zero. This compound may also be called a dibenzo[d,d]dithieno[2,3-b:2',3'-b]thiophene.

In some embodiments, $R_1$ and $R_2$ are the same. In other embodiments, $R_1$ and $R_2$ are independently alkyl.

In additional embodiments, m and n are the same. Specifically, m and n may both be 1.

The semiconducting compound may have the structure of Formula (III):

Formula (III)

wherein $R_3$ and $R_4$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen.

In specific embodiments, $R_3$ and $R_4$ are identical and are selected from alkyl, substituted alkyl, alkenyl, substituted alkenyl, alkynyl, substituted alkynyl, aryl, substituted aryl, heteroaryl, and substituted heteroaryl.

Also disclosed in embodiments is a semiconductor composition comprising a polymer binder; and a semiconducting compound of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of sidechains and is an integer from 0 to 6; n is the number of $R_2$ sidechains and is an integer from 0 to 6; and p and q are independently 0 or 1.

The polymer binder may be a styrene-based polymer, or an arylamine-based polymer, or a polymer binder selected from a list of polymers as discussed further herein.

The weight ratio of the semiconducting compound to the polymer binder can be from 5:1 to about 2:3.

Also disclosed is an electronic device comprising a semiconducting layer, the semiconducting layer comprising a semiconducting compound of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of sidechains and is an integer from 0 to 6; n is the number of $R_2$ sidechains and is an integer from 0 to 6; and p and q are independently 0 or 1.

The semiconducting layer may further comprise a polymer binder.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The term "room temperature" refers to a temperature in the range of 20° C. to 25° C.

The present disclosure relates to semiconducting compounds as disclosed herein. Compositions comprising the semiconducting compounds are also disclosed. A semiconducting layer including the semiconducting compounds is very stable in air and has high mobility. These semiconducting compounds are useful in electronic devices, such as thin-film transistors (TFTs).

Figure 1:
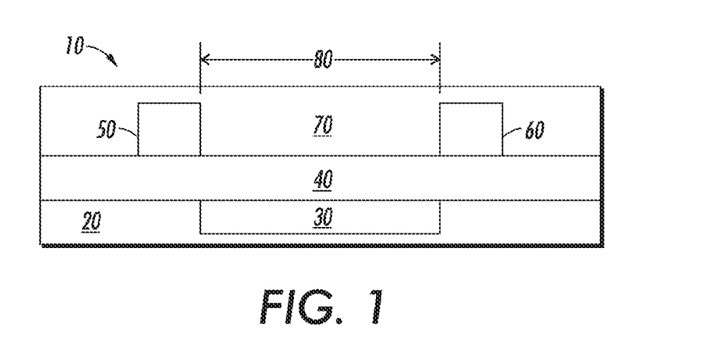
FIG. 1 is a diagram of a first embodiment of a TFT according to the present disclosure.

FIG. 1 illustrates a bottom-gate bottom-contact TFT configuration according to the present disclosure. The TFT 10 comprises a substrate 20 in contact with the gate electrode 30 and a gate dielectric layer 40. The gate electrode 30 is depicted here in a depression within the substrate 20, but the gate electrode could also be located atop the substrate. It is important that the gate dielectric layer 40 separates the gate electrode 30 from the source electrode 50, drain electrode 60, and the semiconducting layer 70. The semiconducting layer 70 runs over and between the source and drain electrodes 50 and 60. The semiconductor has a channel length 80 between the source and drain electrodes 50 and 60.

Figure 2:
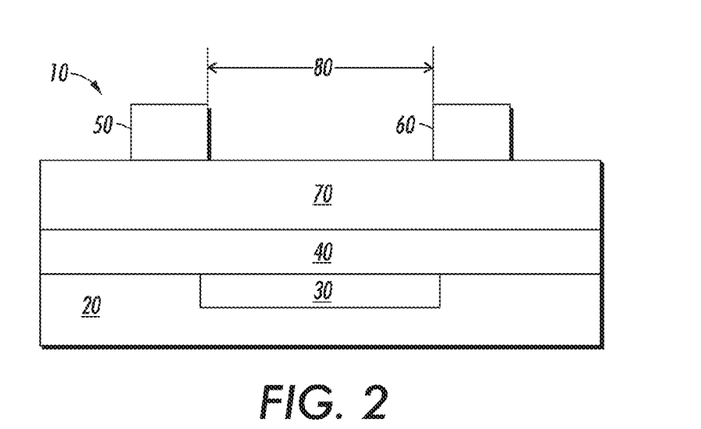
FIG. 2 is a diagram of a second embodiment of a TFT according to the present disclosure.

FIG. 2 illustrates another bottom-gate top-contact TFT configuration according to the present disclosure. The TFT 10 comprises a substrate 20 in contact with the gate electrode 30 and a gate dielectric layer 40. The semiconducting layer 70 is placed on top of the gate dielectric layer 40 and separates it from the source and drain electrodes 50 and 60.

Figure 3:
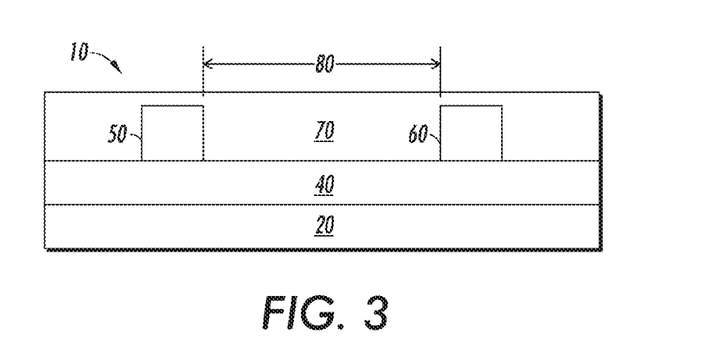
FIG. 3 is a diagram of a third embodiment of a TFT according to the present disclosure.

FIG. 3 illustrates a bottom-gate bottom-contact TFT configuration according to the present disclosure. The TFT 10 comprises a substrate 20 which also acts as the gate electrode and is in contact with a gate dielectric layer 40. The source electrode 50, drain electrode 60, and semiconducting layer 70 are located atop the gate dielectric layer 40.

Figure 4:
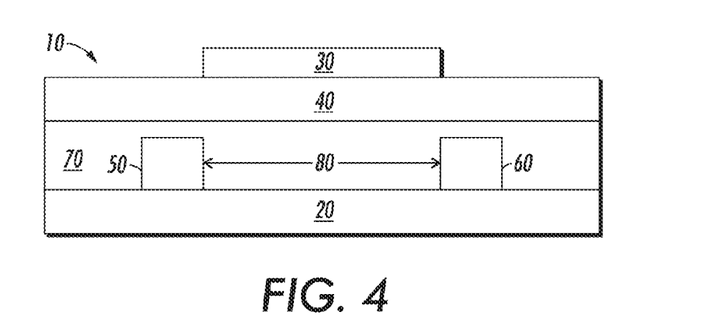
FIG. 4 is a diagram of a fourth embodiment of a TFT according to the present disclosure.

FIG. 4 illustrates a top-gate top-contact TFT configuration according to the present disclosure. The TFT 10 comprises a substrate 20 in contact with the source electrode 50, drain electrode 60, and the semiconducting layer 70. The semiconducting layer 70 runs over and between the source and drain electrodes 50 and 60. The gate dielectric layer 40 is on top of the semiconducting layer 70. The gate electrode 30 is on top of the gate dielectric layer 40 and does not contact the semiconducting layer 70.

In more specific embodiments, the semiconducting compound of the present disclosure has the structure of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 6; n is the number of $R_2$ sidechains and is an integer from 0 to 6; and p and q are independently zero or 1. The values of p and q determine whether the compound contains a phenyl ring or a naphthalene ring. The compound of Formula (I) is a diaryl[d,d']dithieno[2,3-b;2',3'-b']thiophene, and may also be referred to herein as "DADTT".

In more specific embodiments, the semiconducting compound of the present disclosure has the structure of Formula (II):

Formula (II)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 4; and n is the number of $R_2$ sidechains and is an integer from 0 to 4. The compound of Formula (II) is a dibenzo[d,d']dithieno[2,3-b:2',3'-b]thiophene, and may also be referred to herein as "DBDTT".

The term "alkyl" refers to a radical composed entirely of carbon atoms and hydrogen atoms which is fully saturated and of the formula $—C_nH_{2n+1}$. The alkyl radical may be linear, branched, or cyclic.

The term "alkenyl" refers to a radical composed entirely of carbon atoms and hydrogen atoms which contains at least one carbon-carbon double bond that is not part of an aryl or heteroaryl structure. The radical may be linear, branched, or cyclic.

The term "alkynyl" refers to a radical composed entirely of carbon atoms and hydrogen atoms which contains at least one carbon-carbon triple bond. The alkynyl radical may be linear, branched, or cyclic.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to an aromatic radical composed of carbon atoms, hydrogen atoms, and one or more heteroatoms. The carbon atoms and the heteroatoms are present in a cyclic ring or backbone of the radical. The heteroatoms are selected from O, S, and N. Exemplary heteroaryl radicals include thienyl and pyridyl.

The term "alkoxy" refers to an alkyl radical which is attached to an oxygen atom, i.e.—$O—C_nH_{2n+1}$.

The term "alkylthio" refers to an alkyl radical which is attached to a sulfur atom, i.e. —$S—C_nH_{2n+1}$.

The term "substituted" refers to at least one hydrogen atom on the named radical being substituted with another functional group, such as halogen, —CN, —$NO_2$, —COOH, and —$SO_3H$. An exemplary substituted alkyl group is a perhaloalkyl group, wherein one or more hydrogen atoms in an alkyl group are replaced with halogen atoms, such as fluorine, chlorine, bromine, and iodine. Besides the aforementioned functional groups, an aryl or heteroaryl group may also be substituted with alkyl or alkoxy or alkylthio. Exemplary substituted aryl groups include methylphenyl and methoxyphenyl. Exemplary substituted heteroaryl groups include dodecylthienyl.

Generally, the alkyl, alkoxy, and alkylthio groups each independently contain from 1 to 30 carbon atoms, including from about 4 to about 16 carbon atoms. Similarly, the aryl groups independently contain from 6 to 30 carbon atoms. Heteroaryl groups independently contain from 4 to 30 carbon atoms. In specific embodiments, aryl and heteroaryl groups are substituted with an alkyl group having from about 3 to about 16 carbon atoms.

In embodiments, the semiconducting compound has a high band gap which is greater than 2.3 eV. This large band gap typically means that the semiconducting compound has better stability in air, when compared to a pentacene-based semiconductor. The semiconducting compound has a crystalline or liquid-crystalline structure.

In some specific embodiments of Formula (I) and Formula (II), $R_1$ and $R_2$ are the same sidechain, m=1, and n=1. In other specific embodiments, $R_1$ and $R_2$ are alkyl. In specific embodiments of Formula (I), p and q are identical (i.e. either both are zero or both are 1).

In more specific embodiments, the semiconducting compound has the structure of Formula (III):

Formula (III)

wherein $R_3$ and $R_4$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen. Here, there are two R sidechains, located in the 2- and 7-positions.

In some specific embodiments, $R_3$ and $R_4$ are identical and are selected from alkyl, alkenyl, alkynyl, and aryl. In other embodiments, $R_3$ and $R_4$ are identical and are selected from alkyl, substituted alkyl, alkenyl, substituted alkenyl, alkynyl, substituted alkynyl, aryl, substituted aryl, heteroaryl, and substituted heteroaryl.

Various methods known in the art can be used to make the semiconducting compounds described herein. For example, Scheme 1 shows a first approach. This starts with commercially available 3-bromobenzothiophene 1, which can undergo a lithium-halogen exchange reaction with alkyllithium reagents, followed by transmetallation with anhydrous zinc chloride. This zinc anion 2 can then undergo a Negishi cross-coupling reaction with a 2,3-dibromobenzothiophene 3 regioselectively at the more reactive 2-position. This intermediate 4 can then be converted to the dianion with an alkyllithium reagent and quenched with an electrophilic sulfur source such as diphenylsulfonyl sulfide to form the third thiophene ring of the DADTT core 5.

Scheme 1

Scheme 2 shows the addition of alkyl substituents to a DADTT core, which is shown here as a DBDTT core 5. First, the DBDTT core 5 is reacted with a substituted acid chloride in the presence of aluminum trichloride to form a diketonyl DBDTT 6. Next, the diketonyl DBDTT 6 is deoxygenated using a modified Wolff-Kishner reduction using hydrazine in the presence of potassium hydroxide in diethylene glycol. This forms the dialkyl-DBDTT 7. More than one acid chloride may be used to obtain compounds having two or more different R sidechains.

Scheme 2

Aryl substituents can be added by first brominating the DBDTT core 5 with bromine. The intermediate brominated compound 8 can then be acrylated using standard palladium-catalyzed cross-coupling techniques. Scheme 3 uses a Suzuki-Miyaura coupling as a representative example, with boron complex 9 reacting to form the diaryl-DBDTT 10. More than boron complex may be used to obtain compounds having two or more different aryl sidechains.

Scheme 3 wherein $R^g$, $R^h$, $R^j$, and $R^k$ are independently selected from hydrogen, halogen, and $C_1$-$C_{20}$ alkyl; and n is an integer from 0 to 5. The styrene monomer can be styrene ($R^g$, $R^h$, and $R^j$ are all hydrogen, n=0), alpha-methyl styrene ($R^g$ is methyl, $R^h$ and $R^j$ are hydrogen, n=0), or 4-methyl styrene ($R^g$, $R^h$, and $R^j$ are all hydrogen, n=1, $R^k$ is methyl in the 4-position). The term "styrene-based polymer" is intended to encompass both homopolymers and copolymers. The term "copolymer" is intended to encompass random and block copolymers.

The semiconducting compound by itself has poor film-forming properties, which is attributed to its crystalline or liquid-crystalline nature. Thus, the semiconducting layer is typically formed from a semiconductor composition that comprises the semiconducting compound and a polymer binder, which allows a uniform film to be achieved, significantly improving device performance. The polymer binder can be considered as forming a matrix within which the semiconducting compound is dispersed.

Any suitable polymer can be used as the polymer binder for the semiconductor composition. In some embodiments, the polymer is an amorphous polymer. The amorphous polymer may have a glass transition temperature less than the melting point temperature of the semiconducting compound. In other embodiments, the amorphous polymer has a glass transition temperature greater than the melting point temperature of the semiconducting compound. In embodiments, the polymer has a dielectric constant less than 4.5, preferably less than 3.5, including less than 3.0, as measured at 60 Hz at room temperature. In embodiments, the polymer is selected from polymers containing only C, H, F, Cl, or N atoms. In some embodiments, the polymer is a low polarity polymer, such as a hydrocarbon polymer or a fluorocarbon polymer without any polar groups. For example, polystyrene is an amorphous polymer and has a dielectric constant about 2.6. A list of other low polarity polymers includes but is not limited to the following: fluoropolyarylether, poly(p-xylylene), poly(vinyl toluene), poly (alpha-methyl styrene), poly(alpha-vinylnaphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane) bis-(4-phenyl) carbonate], poly(α-α-α'-α' tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-α-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isoprene-block-styrene), terpene resin, poly(N-vinylcarbazole), polycarbazole, polytriarylamine, and the like.

In particular embodiments, the polymer binder is a styrene-based polymer. Styrene-based polymers contain a repeating unit derived from a styrene monomer of Formula (a):

In other particular embodiments, the polymer binder is an arylamine-based polymer. An arylamine-based polymer has a repeating unit derived from a monomer having the structure of Formula (b), Formula (c) or Formula (d):

wherein $R^m$, $R^n$, $R^p$, $R^q$, and $R^r$ are independently selected from hydrogen, halogen, $C_1$-$C_{20}$ alkyl, and aryl; p' and q' are independently an integer from 0 to 5; and $R^w$ is selected from $C_1$-$C_{20}$ alkyl, aryl, and substituted aryl. The term "arylamine-based" polymers is intended to encompass poly(N-vinyl carbazole), polycarbazole, and triarylamine-based polymers.

In specific embodiments, the styrene-based polymer and the arylamine-based polymer include polystyrene, poly(α-methyl styrene), poly(4-methyl styrene), poly(vinyl toluene), poly(α-methyl styrene-co-vinyl toluene), poly(styrene-block-butadiene-block-styrene), poly(styrene-block-isoprene-block-styrene), a terpene resin, poly(styrene-co-2,4-dimethylstyrene), poly(chlorostyrene), poly(styrene-co-α-methyl styrene), poly(styrene/butadiene), poly(N- vinylcarbazole), polycarbazole, and polytriarylamines. It should be noted that one or more polymer binders can be used in the semiconductor composition.

Generally, the polymer binder may have a weight average molecular weight of from about 10,000 to about 2,000,000, including from about 40,000 to about 1,000,000. In more specific embodiments, the polymer binder is a styrene-based polymer. In particular embodiments, the styrene-based polymer has a weight average molecular weight of from about 40,000 to about 2,000,000. In some embodiments, the styrene-based polymer has a molecular weight of from about 100,000 to about 1,000,000. In one preferred embodiment, the polymer binder is polystyrene, poly(alpha-methyl styrene), or poly(4-methyl styrene) having a weight average molecular weight of from about 40,000 to about 2,000,000.

The weight ratio of the semiconducting compound of Formula (I) to the polymer binder may be from about 99:1 to about 1:3, including from about 10:1 to about 1:2, from about 5:1 to about 2:3, or from about 3:2 to about 3:4. In some embodiments, the weight ratio of the semiconducting compound of Formula (I) to the polymer binder is around 1:1.

The semiconductor composition may further comprise a solvent in which the semiconducting compound and the polymer binder are soluble. Exemplary solvents used in the solution may include chlorinated solvents such as chlorobenzene, chlorotoluene, dichlorobenzene, dichloroethane, chloroform, trichlorobenzene, and the like; alcohols and diols such as propanol, butanol, hexanol, hexanediol, etc.; hydrocarbons or aromatic hydrocarbons such as hexane, heptane, toluene, decalin, xylene, ethyl benzene, tetrahydronaphthalene, methyl nanphthalene, mesitylene, trimethyl benzene, etc.; ketones such as acetone, methyl ethyl ketone, etc.; acetates, such as ethyl acetate; pyridine, tetrahydrofuran, and the like.

The semiconducting compound and the polymer binder are from about 0.05 to about 20 weight percent of the semiconductor composition, including from about 0.1 to about 10 weight percent of the semiconductor composition, or from about 0.1 to about 1.0 weight percent of the semiconductor composition.

In embodiments, the semiconductor composition comprising the semiconducting compound and the polymer binder may have a viscosity of from about 1.5 centipoise (cps) to about 100 cps, including from about 2 to about 20 cps. The use of a high molecular weight polymer binder will increase the viscosity of the semiconductor composition. As a result, it will help to form a uniform semiconductor layer upon using solution deposition techniques such as inkjet printing and spin coating.

Bottom-gate TFTs may be advantageous because they are generally simpler to fabricate. However, previous semiconductor/polymer composite systems have only achieved high mobility in top-gate devices. When the semiconductor composition of the present disclosure is utilized, high mobility can also be achieved in bottom-gate devices like those shown in FIGS. 1-3.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like.

After being deposited, the semiconductor composition is optionally thermally treated (for example, by drying or annealing) at an elevated temperature which is lower than the melting point of the semiconducting compound used in the semiconductor composition. Depending on the semiconducting compound used, the temperature of the thermal treatment may vary. For example, the thermal treatment may be carried out at a temperature of less than 200° C., less than 150° C., or less than 100° C. Generally, the semiconductor layer will not undergo a thermal treatment process having a temperature higher than the melting point of the semiconducting compound. In some embodiments, particularly those which use the semiconducting compound of Formula (I), there is absent of an annealing step during the fabrication of a semiconductor layer from the semiconductor composition. Annealing at a temperature higher than the melting point of the semiconducting compound would cause significant phase separation of the semiconducting compound and the polymer binder, as well as increasing the average crystal size of the semiconducting compound. As a result, the electronic device would show poor electrical performance.

In particular embodiments, the semiconducting compound of the present disclosure is crystalline, particularly at room temperature, and has an average crystal size in the semiconducting layer of 100 nanometers or less. In specific embodiments, the average crystal size is 50 nanometers or less. In more specific embodiments, the average crystal size is 35 nanometers or less. The crystalline semiconducting compound generally has a crystal size greater than 5 nanometers. The average crystal size can be measured using methods such as X-ray diffraction, transmission electron microscopy (TEM), scanning electron microscopy (SEM), atomic force microscopy (AFM), etc. The measurement of the average crystal size is expressed as the diameter of a spherical volume. However, this should not be construed as requiring the crystals of the semiconducting compound to have a particular morphology or shape.

The semiconducting layer formed using the semiconductor composition can be from about 5 nanometers to about 1000 nanometers deep, including from about 20 to about 100 nanometers in depth. In certain configurations, such as the configurations shown in FIG. 1, the semiconducting layer completely covers the source and drain electrodes.

The performance of a TFT can be measured by mobility. The mobility is measured in units of $cm^2/N \cdot sec$; higher mobility is desired. The resulting TFT including the semiconducting compound of the present disclosure may have a field effect mobility of at least 0.1 $cm^2/N \cdot sec$, including at least 0.2 $cm^2/N \cdot sec$, or at least 0.5 $cm^2/N \cdot sec$. The TFT of the present disclosure may have a current on/off ratio of at least $10^4$, including at least $10^5$, or at least $10^6$.

The thin film transistor generally also includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. The two semiconducting layers can be directly contacted with this modified dielectric layer surface. The contact may be complete or partial. This surface modification can also be considered as forming an interfacial layer between the dielectric layer and the semiconducting layer. In particular embodiments, the surface of the dielectric layer has been modified with an organosilane agent of Formula (A):

$$(L)_t[SiR_m(R')_{4-m-t}]_v \qquad \text{Formula (A)}$$

wherein R is alkyl, substituted alkyl, aryl, or substituted aryl containing from 1 to about 20 carbon atoms, R' is halogen or alkoxy; m is an integer from 1 to 4; L is a linking atom; t is 0 or 1, and indicates whether a linking atom is present; and v indicates the number of trisubstitutedsilyl groups on the linking atom. The sum of (m+t) is never greater than 4. When t is 0, v is automatically 1. Exemplary organosilanes include octyltrichlorosilane (OTS-8) (t=0, R=octyl, m=1, R'=chloro, v=1), dodecyltrichlorosilane, octadecyltrichlorosilane, hexamethyldisilazane (HMDS) (L=NH, t=1, R=methyl, m=3, v=2), phenyltrichlorosilane, methyltrimethoxylsilane, phenylmethyldimethoxysilane, phenylmethyldichlorosilane, (3-phenylpropyl)dimethylchlorosilane, (3-phenylpropyl)methyldichlorosilane, phenyltrimethoxysilane, phenethyltrichlorosilane, and the like. In specific embodiments, the R comprises a phenyl group. Other surface modifiers such as polystyrene, polysiloxane, or polysilsesquioxane can be used as well.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers.

The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconductor layer are on the substrate, even though one layer is closer to the substrate than the other layer. The resulting TFT has good mobility and good current on/off ratio.

The following examples are for purposes of further illustrating the present disclosure. The examples are merely illustrative and are not intended to limit devices made in accordance with the disclosure to the materials, conditions, or process parameters set forth therein. All parts are percentages by volume unless otherwise indicated.

Example

Molecular modeling studies were performed for the compound labeled DBDTT-C5, which corresponds to Formula (II) when $R_3$ and $R_4$ are —$C_5H_{11}$. Molecular modeling studies were also performed for the compound labeled DNDTT-C5, which corresponds to Formula (I) when p and q are both 1, and $R_1$ and $R_2$ are —$C_5H_{11}$ and are located at the 3- and 9-positions. DNDTT-C5 has the formal name of 3,10-dipentyl-dinaphtho[d,d']dithieno[2,3-b:2',3'-b]thiophene.

DBDTT-C5 and DNDTT-C5 were then compared to the comparative compound labeled 1-C5, which is shown below and is symmetrical. The model was formed in Materials Studio 5.0 using the DMol3 package to determine equilibrium geometry using density functional methods (PBE) and then completing a single-point energy calculation on the optimized structure (HCTH).

DBDTT-C5

DNDTT-C5

1-C5

Table 1 lists the results. These indicate that the three compounds have similar electronic properties and should have a similar charge-transporting ability.

TABLE 1

|  | DBDTT-C5 | DNDTT-C5 | 1-C5 (comparative) |
|---|---|---|---|
| HOMO (eV) | −4.89 | −4.748 | −4.95 |
| LUMO (eV) | −1.89 | −2.379 | −2.20 |
| Band Gap (eV) | 3.00 | 2.37 | 2.75 |

Figure 5:
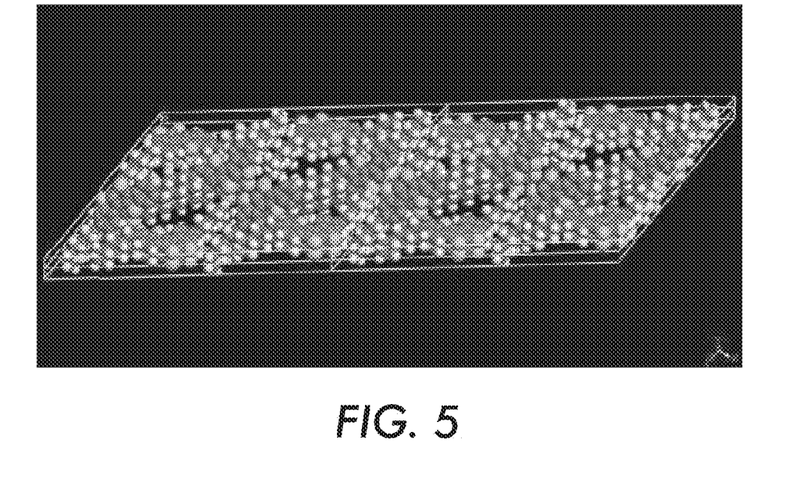
FIG. 5 shows a color model of the equilibrium geometry and crystal structure of a dialkyl-substituted dibenzodithienothiophene calculated using molecular modeling techniques.
Figure 6:
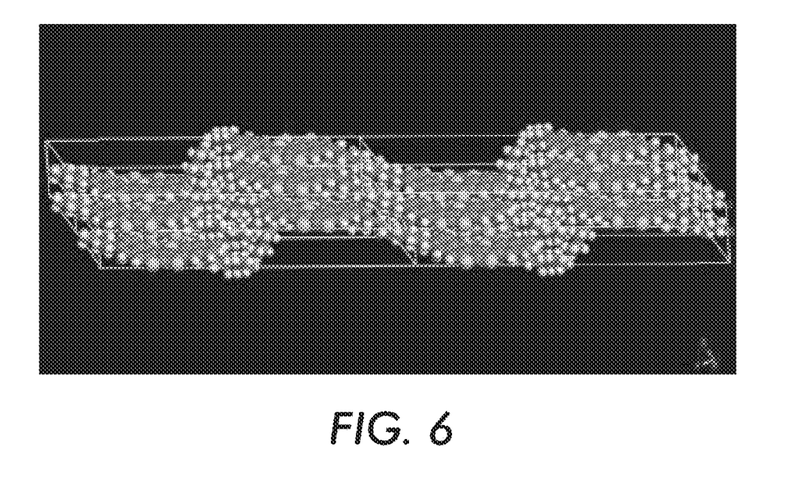
FIG. 6 shows a color model of the equilibrium geometry and crystal structure of a dialkyl-substituted dinaphthodithienothiophene calculated using molecular modeling techniques.

The crystallization of DBDTT-C5 and DNDTT-C5 were then simulated using the Polymorph module (COMPASS forcefield). FIG. 5 is a color model showing the solid-state structure of the DBDTT-C5. FIG. 6 is a color model showing the solid-state structure of DNDTT-C5. Both molecules aligned in stacks due to π-π stacking, which facilitates hole transport. In particular, the sulfur atoms aligned with each other. The alkyl chains are aligned parallel to the aromatic stacks and should provide longer range order in the solid state. This indicates that these two molecules can each form a crystal polymorph which should be suitable for efficient charge transport.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A semiconducting compound having the structure of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 6; n is the number of $R_2$ sidechains and is an integer from 0 to 6; and p and q are independently 0 or 1.

2. The semiconducting compound of claim 1, wherein the semiconducting compound has the structure of Formula (II):

Formula (II)

wherein m and n are independently an integer from 0 to 4.

3. The semiconducting compound of claim 1, wherein $R_1$ and $R_2$ are independently alkyl.

4. The semiconducting compound of claim 1, wherein m and n are 1.

5. The semiconducting compound of claim 1, wherein the semiconducting compound has the structure of Formula (III):

Formula (III)

wherein $R_3$ and $R_4$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen.

6. The semiconducting compound of claim 5, wherein $R_3$ and $R_4$ are identical and are selected from alkyl, substituted alkyl, alkenyl, substituted alkenyl, alkynyl, substituted alkynyl, aryl, substituted aryl, heteroaryl, substituted and heteroaryl.

7. A semiconductor composition comprising:
a polymer binder; and
a semiconducting compound of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 6; n is the number of $R_2$ sidechains and is an integer from 0 to 6; and p and q are independently 0 or 1.

8. The semiconductor composition of claim 7, wherein the semiconducting compound has the structure of Formula (II):

Formula (II)

wherein m and n are independently an integer from 0 to 4.

9. The semiconductor composition of claim 7, wherein m and n are 1.

10. The semiconductor composition of claim 7, wherein the semiconductor composition has the structure of Formula (III):

Formula (III)

wherein $R_3$ and $R_4$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen.

11. The semiconductor composition of claim 10, wherein $R_3$ and $R_4$ are identical and are selected from alkyl, substituted alkyl, alkenyl, substituted alkenyl, alkynyl, substituted alkynyl, aryl, substituted aryl, heteroaryl, and substituted heteroaryl.

12. The semiconductor composition of claim 7, wherein the polymer binder is selected from the group consisting of fluoropolyarylether, poly(p-xylylene), poly(vinyl toluene), poly(α-methyl styrene), poly(a-vinylnaphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane)bis-(4-phenyl) carbonate], poly(α-α-α'-α'-tetrafluoro-p-xylylene), fluorinated polyimide, poly (ethylene/tetrafluoroethylene), poly(ethylene/chlorotrifluoroethylene), fluorinated ethylene/propylene copolymer, poly(styrene-co-α-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isoprene-block-styrene), terpene resin, poly(N-vinylcarbazole), polycarbazole, and polytriarylamine.

13. The semiconductor composition of claim 7, wherein the polymer binder is a styrene-based polymer or an arylamine-based polymer.

14. The semiconductor composition of claim 7, wherein the weight ratio of the semiconducting compound to the polymer binder is from 5:1 to about 2:3.

15. An electronic device comprising a semiconducting layer, the semiconducting layer comprising a semiconducting compound of Formula (I):

Formula (I)

wherein each $R_1$ and $R_2$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen; m is the number of $R_1$ sidechains and is an integer from 0 to 6; n is the number of $R_2$ sidechains and is an integer from 0 to 6; and p and q are independently 0 or 1.

16. The electronic device of claim 15, wherein the semiconducting compound has the structure of Formula (II):

Formula (II)

wherein m and n are independently an integer from 0 to 4.

17. The electronic device of claim 15, wherein the electronic device has the structure of Formula (III):

Formula (III)

wherein $R_3$ and $R_4$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, cyano (CN), and halogen.

18. The electronic device of claim 17, wherein $R_3$ and $R_4$ are identical and are selected from alkyl, substituted alkyl, alkenyl, substituted alkenyl, alkynyl, substituted alkynyl, aryl, substituted aryl, heteroaryl, and substituted heteroaryl.

19. The electronic device of claim 15, wherein the semiconducting layer further comprises a polymer binder.

20. The electronic device of claim 19, wherein the polymer binder is selected from the group consisting of fluoropolyarylether, poly(p-xylylene), poly(vinyl toluene), poly(α-methyl styrene), poly(a-vinylnaphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane) bis-(4-phenyl) carbonate], poly(α-α-α'-α'-tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-α-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isoprene-block-styrene), terpene resin, poly(N-vinylcarbazole), polycarbazole, and polytriarylamine.

* * * * *